US009862655B2

(12) United States Patent
Fichtl et al.

(10) Patent No.: US 9,862,655 B2
(45) Date of Patent: Jan. 9, 2018

(54) METHODS AND SYSTEMS FOR PRODUCING JET-RANGE HYDROCARBONS

(71) Applicant: UOP LLC, Des Plaines, IL (US)

(72) Inventors: Geoffrey William Fichtl, Chicago, IL (US); James M. Anderson, Elmhurst, IL (US); Michael J. McCall, Geneva, IL (US)

(73) Assignee: UOP LLC, Des Plaines, IL (US)

( * ) Notice: Subject to any disclaimer, the term of this patent is extended or adjusted under 35 U.S.C. 154(b) by 72 days.

(21) Appl. No.: 14/319,017

(22) Filed: Jun. 30, 2014

(65) Prior Publication Data

US 2015/0376089 A1    Dec. 31, 2015

(51) Int. Cl.
    *C07C 5/03*    (2006.01)
    *C07C 2/04*    (2006.01)
    (Continued)

(52) U.S. Cl.
    CPC .............. *C07C 5/03* (2013.01); *B01D 3/009* (2013.01); *C07C 1/24* (2013.01); *C07C 2/12* (2013.01);
    (Continued)

(58) Field of Classification Search
    CPC ....................................................... C10L 1/16
    (Continued)

(56) References Cited

U.S. PATENT DOCUMENTS 4,482,772 A * 11/1984 Tabak ...................... C07C 1/20
                                                585/254
5,990,367 A * 11/1999 Stine ....................... C07C 2/08
                                                585/502
(Continued)

FOREIGN PATENT DOCUMENTS

CN      101711274 B       6/2013
WO      EP 0178846 A2 *   4/1986    ............. C01B 37/02
(Continued)

OTHER PUBLICATIONS

Search Report dated Oct. 8, 2015 for corresponding PCT Appl. No. PCT/US2015/038435.
(Continued)

*Primary Examiner* — In Suk Bullock
*Assistant Examiner* — Youngsul Jeong

(57) ABSTRACT

Methods and systems for producing jet-range hydrocarbons are disclosed herein. In an exemplary embodiment, a method for producing jet-range hydrocarbons includes the steps of combining a first stream including C4 olefinic hydrocarbons and a second stream including C5-C8 olefinic hydrocarbons to produce a third stream including C4-C8 hydrocarbons, oligomerizing the third stream including C4-C8 olefinic hydrocarbons to produce a fourth stream including C4-C20 olefinic hydrocarbons, and separating C5-C8 hydrocarbons from the fourth stream including C4-C20 olefinic hydrocarbons to produce the second stream including C5-C8 olefinic hydrocarbons and a fifth stream including C9-C20 olefinic hydrocarbons. The method further includes the step of hydrogenating the fifth stream including C9-C20 olefinic hydrocarbons to produce a sixth stream including C9-C20 paraffinic jet-range hydrocarbons.

5 Claims, 1 Drawing Sheet

(51) Int. Cl.

| | |
|---|---|
| *C07C 2/06* | (2006.01) |
| *C07C 2/08* | (2006.01) |
| *C07C 2/12* | (2006.01) |
| *C10L 1/16* | (2006.01) |
| *B01D 3/00* | (2006.01) |
| *C10L 1/04* | (2006.01) |
| *C07C 1/24* | (2006.01) |
| *C10G 50/00* | (2006.01) |
| *C10G 69/12* | (2006.01) |
| *C10G 3/00* | (2006.01) |

(52) U.S. Cl.
CPC ............... *C10G 3/00* (2013.01); *C10G 50/00* (2013.01); *C10G 69/126* (2013.01); *C10L 1/04* (2013.01); *C07C 2529/70* (2013.01); *C10G 2400/08* (2013.01); *Y02P 20/127* (2015.11)

(58) Field of Classification Search
USPC ......................................................... 585/14
See application file for complete search history.

(56) References Cited

U.S. PATENT DOCUMENTS

| | | | |
|---|---|---|---|
| 8,395,007 | B2 | 3/2013 | Wright et al. |
| 2005/0274063 | A1 | 12/2005 | Forester et al. |
| 2011/0113679 | A1 | 5/2011 | Cohen et al. |
| 2011/0288352 | A1* | 11/2011 | Peters ............... C10G 3/42 585/14 |
| 2014/0051897 | A1 | 2/2014 | Peters et al. |

FOREIGN PATENT DOCUMENTS

| | | |
|---|---|---|
| WO | 2013162573 A1 | 10/2013 |
| WO | 2014008337 A1 | 1/2014 |
| WO | 2014074999 A1 | 5/2014 |

OTHER PUBLICATIONS

Wright, Biomass to Alcohol to Jet/Diesel, Presentation; Naval Air Systems, Australia.

* cited by examiner

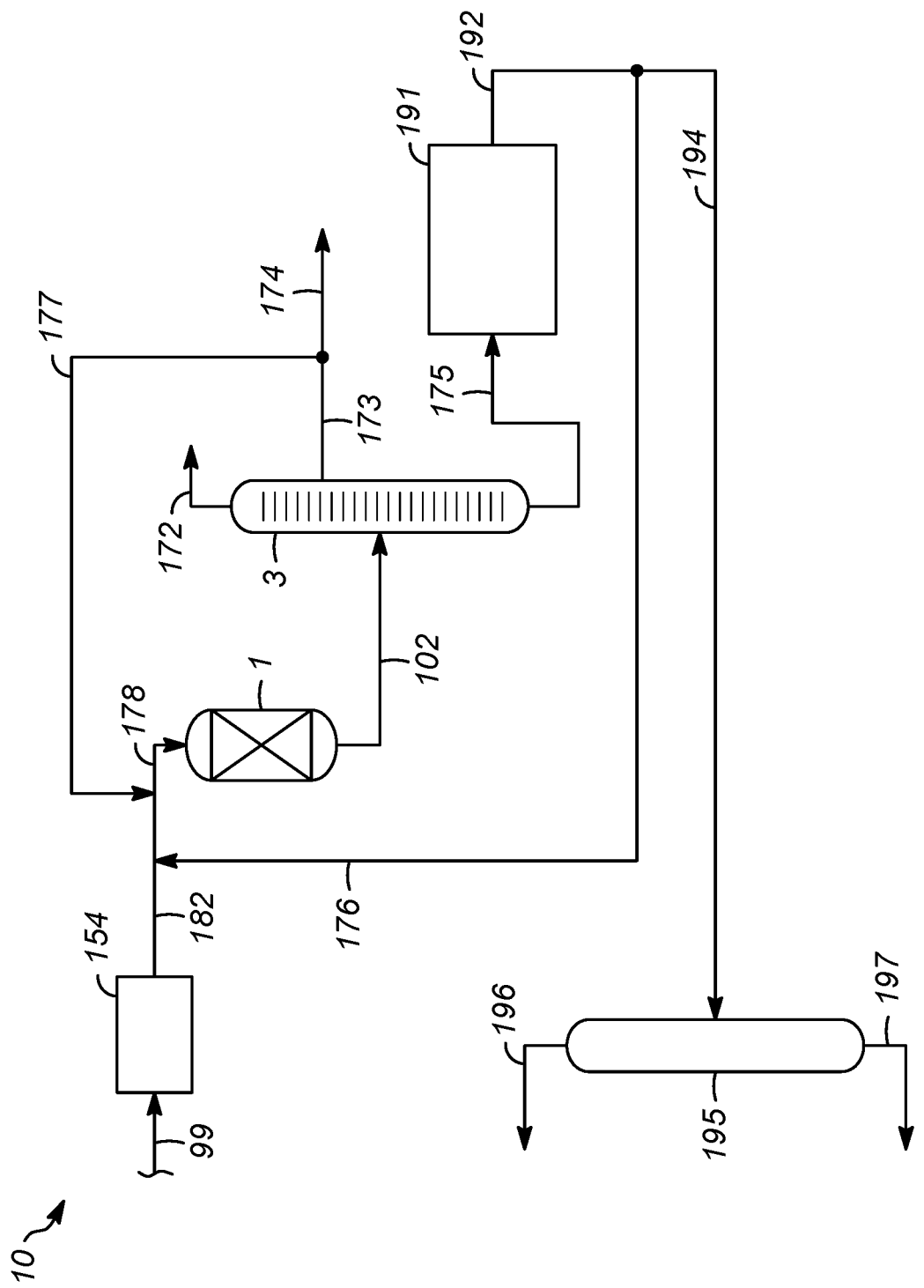

METHODS AND SYSTEMS FOR PRODUCING JET-RANGE HYDROCARBONS

FIELD OF THE INVENTION

The present disclosure generally relates to methods and systems for producing renewable fuels and chemicals from biorenewable sources and the renewable fuels and chemicals produced thereby, and more particularly relates to methods and systems for producing jet-range hydrocarbons ("jet fuel") from alkanols, including for example isobutanol, and the jet-range hydrocarbons produced thereby.

DESCRIPTION OF RELATED ART

As the worldwide demand for fuel increases, interest in sources other than crude oil from which to produce transportation fuels, including aviation fuels, is ever increasing. For example, due to the growing environmental concerns over fossil fuel extraction and economic concerns over exhausting fossil fuel deposits, there is a demand for using an alternate or "green" feed source for producing hydrocarbons for use as transportation fuels and for use in other industries. Such sources of interest include, for example, biorenewable sources, such as vegetable and seed oils, animal fats, and algae byproducts, among others as are well-known to those skilled in the art. A conventional catalytic hydro-processing technique is known for converting a biorenewable feedstock into green diesel fuel that may be used as a substitute for the diesel fuel produced from crude oil. As used herein, the terms "green diesel fuel" and "green jet fuel" refer to fuel produced from biorenewable sources, in contrast to those produced from crude oil. The process also supports the possible co-production of propane and other light hydrocarbons, as well as naphtha or green jet fuel.

Acceptance of fuels produced from biorenewable sources in the aviation industry has, to date, been slower than desirable. In some instances, the fatty acids from vegetable and seed oils used in the conventional catalytic hydro-processing techniques noted above may have several specific disadvantages compared to petroleum-derived fuels. For aviation engines, such as gas turbine engines, the cold flow properties of the long-chain fatty esters from vegetable and seed oils may, in some instances, be sufficiently poor so as to cause operational problems, even when used at levels in the fuel as low as about 5% by weight. Under cold conditions, the precipitation and crystallization of fatty paraffin waxes has the potential to cause flow and filter plugging problems. Further, the high temperature instability of, for example, the esters and olefinic bonds in vegetable and seed oils is also a potential problem.

To avoid the problems that are sometimes encountered in using biorenewable fatty acids and the like as the feedstock for the production of green fuels, alternative production schemes using isoalkanols, such as for example isobutanol, as feedstocks have been proposed. Renewable isoalkanols are typically formed by fermentation. For example, the feedstock for the fermentation process can be any suitable fermentable feedstock known in the art, such as sugars derived from agricultural crops including sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). In order to produce jet-range fuels from isoalkanols, in one example known in the art, isobutanol is first dehydrated to form butenes. The butenes are then oligomerized to preferentially form trimers, tetramers, and sometimes pentamers of isobutene, i.e. $C_{12}$, $C_{16}$, and sometimes $C_{20}$ olefins. Finally, the olefins are hydrogenated to form $C_{12}$, $C_{16}$, and $C_{20}$ paraffins. This process is commonly known as an alcohol-to-jet fuel ("ATJ") process.

The flash point of any jet fuel, whether obtained from fossil fuels or biorenewable sources, is an important specification to ensure safe handling of the jet fuel from production to end use in a turbine engine. The flash point in refining processes in commonly controlled by fractionation of the hydrocarbon stream to reject from the jet fraction the volatile "light" components that generally cause the jet fuel flash point to be too low to comply with specifications. For example, a typical jet fuel flash point specification, per ASTM D1655 and D7566, is 38° C. when measured in accordance with the ASTM D56 testing protocol, as promulgated by ASTM International, Inc. of West Conshohocken, Pa. However, in some applications, jet fuels are required to have a higher flash point of 60° C. in accordance with the ASTM D93 testing protocol. These applications include, for example, JP-5 U.S. Navy jet fuel, per MIL-DTL-5624U.

The production of high-flash point jet fuel from conventional fossil fuel sources is challenging because often, rejection of the volatile light components via fractionation to meet the flash point target has an adverse effect on other jet fuel properties, such as the freeze point. In the case of JP-5, the freeze point specification is only slightly relaxed relative to JP-8 or Jet A-1, from −47° C. to −46° C. Accordingly, the typical result is that JP-5 is produced with much lower yield than JP-8 or Jet A-1. This lower yield is due to three main effects: 1. The conversion process unit producing the jet fuel must operate at greater severity to produce a hydrocarbon effluent stream suitable for making JP-5. Frequently, higher severity operation results in increased yield loss due to increased cracking. 2. In the fractionation process, the initial boiling point of the jet fuel must be adjusted upward to comply with the high flash point specification by rejecting volatile light components into a naphtha stream. 3. Due to reason 2, the final boiling point of the jet fuel typically needs to be decreased via fractionation to reject heavy compounds that cause freeze point problems into the heavier diesel product.

Accordingly, it is desirable to provide methods and systems for producing jet-range fuels from a biorenewable feedstock with a relatively high flash point, but without negative effect on the freeze point. Further, it is desirable to provide such methods and systems that do not suffer from reduced yields. Further still, other desirable features and characteristics of the present disclosure will become apparent from the subsequent detailed description and the appended claims, when taken in conjunction with the accompanying drawing and this background.

SUMMARY OF THE INVENTION

Methods and systems for producing jet-range hydrocarbons are disclosed herein. While these methods and systems find greatest utility in converting feedstocks from alcohols allowing for production of jet fuels from renewable sources, this is not intended to limit the application of the method. The methods can also find utility with conversion of $C_4$ olefins to jet fuel with feedstocks that are derived from petroleum.

In an exemplary embodiment, a method for producing jet-range hydrocarbons includes the steps of combining a first stream including C4 olefinic hydrocarbons and a second stream including C5-C8 olefinic hydrocarbons to produce a third stream including C4-C8 hydrocarbons, oligomerizing the third stream including C4-C8 olefinic hydrocarbons to produce a fourth stream including C4-C20 olefinic hydrocarbons, and separating approximately C5-C8 hydrocarbons from the fourth stream including C4-C20 olefinic hydrocarbons to produce the second stream including C5-C8 olefinic hydrocarbons and a fifth stream including C9-C20 olefinic hydrocarbons. The method further includes the step of hydrogenating the fifth stream including C9-C20 olefinic hydrocarbons to produce a sixth stream including C9-C20 paraffinic jet-range hydrocarbons.

In another exemplary embodiment, a system for producing jet-range hydrocarbons includes a mixing device that combines a first stream including C4 olefinic hydrocarbons and a second stream including C5-C8 olefinic hydrocarbons to produce a third stream including C4-C8 hydrocarbons, an oligomerization reactor that oligomerizes the stream including C4-C8 olefinic hydrocarbons to produce a third stream including C4-C20 olefinic hydrocarbons, and a distillation column that separates approximately C5-C8 hydrocarbons from the third stream including C4-C20 olefinic hydrocarbons to produce the second stream including C5-C8 olefinic hydrocarbons and a fourth stream including C9-C20 olefinic hydrocarbons. The system further includes a hydrogenation reactor that hydrogenates the fourth stream including C9-C20 olefinic hydrocarbons to produce approximately C9-C20 paraffinic jet-range hydrocarbons.

In yet another embodiment, a method for producing jet-range hydrocarbons includes the steps of combining a first stream including C4 olefinic hydrocarbons and a second stream including C5-C10 olefinic hydrocarbons to produce a third stream including C4-C10 hydrocarbons, oligomerizing the third stream including C4-C10 olefinic hydrocarbons to produce a fourth stream including C4-C20 olefinic hydrocarbons, and separating approximately C5-C10 hydrocarbons from the fourth stream including C4-C20 olefinic hydrocarbons to produce the second stream including C5-C10 olefinic hydrocarbons and a fifth stream including C11-C20 olefinic hydrocarbons. The method further includes the step of hydrogenating the fifth stream including C11-C20 olefinic hydrocarbons to produce a sixth stream including C11-C20 paraffinic jet-range hydrocarbons.

This summary is provided to introduce a selection of concepts in a broad and simplified form that are further described below in the detailed description. This summary is not intended to identify or delineate key features or essential features of the claimed subject matter, nor is it intended to be used as an aid in determining the scope of the claimed subject matter.

BRIEF DESCRIPTION OF THE DRAWING

Exemplary embodiments of the present disclosure will hereinafter be described in conjunction with the following drawing FIGURE, wherein like numerals denote like elements, and wherein:

The FIGURE schematically illustrates an exemplary embodiment of a system utilizing a process for producing jet-range hydrocarbons from biorenewable feedstocks.

DEFINITIONS

As used herein, the term "stream" can include various hydrocarbon molecules and other substances. Moreover, the term "stream including Cx hydrocarbons" or "stream including Cx olefins" can include a stream including hydrocarbon or olefin molecules, respectively, with "x" number of carbon atoms, suitably a stream with a majority of hydrocarbons or olefins, respectively, with "x" number of carbon atoms and preferably a stream with at least 75 wt- % hydrocarbons or olefin molecules, respectively, with "x" number of carbon atoms. Moreover, the term "stream including Cx+ hydrocarbons" or "stream including Cx+ olefins" can include a stream including a majority of hydrocarbon or olefin molecules, respectively, with more than or equal to "x" carbon atoms and suitably less than 10 wt- % and preferably less than 1 wt- % hydrocarbon or olefin molecules, respectively, with x−1 or less carbon atoms. Lastly, the term "Cx− stream" can include a stream including a majority of hydrocarbon or olefin molecules, respectively, with less than or equal to "x" carbon atoms and suitably less than 10 wt- % and preferably less than 1 wt- % hydrocarbon or olefin molecules, respectively, with x+1 or greater carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "substantially" can mean an amount of at least generally about 70%, preferably about 80%, and optimally about 90%, by weight, of a compound or class of compounds in a stream.

As used herein, the term "overhead stream" can mean a stream withdrawn at or near a top of a vessel, such as a column.

As used herein, the term "bottom stream" can mean a stream withdrawn at or near a bottom of a vessel, such as a column.

As depicted, process flow lines in the figures can be referred to interchangeably as, e.g., lines, pipes, feeds, gases, products, discharges, parts, portions, or streams.

As used herein, "bypassing" with respect to a vessel or zone means that a stream does not pass through the zone or vessel bypassed although it may pass through a vessel or zone that is not designated as bypassed.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

Furthermore, as used in the present disclosure, the terms "renewably-based" or "renewable" denote that the carbon content of the renewable alcohol (and olefin, di-olefin, etc., or subsequent products prepared from renewable alcohols, olefins, di-olefins, etc. as described herein), is from a "new carbon" source as measured by ASTM test method D6866-05, "Determining the Bio-based Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% bio-based material to give percent bio-based content of the sample. Additionally, "Bio-based materials" are organic materials in which the carbon comes from recently (on the order of centuries) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a bio-based material has a $^{14}C/^{12}C$ isotope ratio greater than 0. Contrarily, a fossil-based material has a $^{14}C/^{12}C$ isotope ratio of about 0. The term "renewable" with regard to compounds such as alcohols or hydrocarbons (olefins, di-olefins, polymers, etc.) also refers to compounds prepared from biomass using thermochemical methods (e. g., Fischer-Tropsch catalysts), biocatalysts (e. g., fermentation), or other processes, for example as described herein.

DETAILED DESCRIPTION

The following detailed description is merely exemplary in nature and is not intended to limit the invention or the application and uses of the invention. As used herein, the word "exemplary" means "serving as an example, instance, or illustration." Any embodiment described herein as "exemplary" is not necessarily to be construed as preferred or as advantageous over other embodiments. Furthermore, there is no intention to be bound by any theory presented in the preceding background or the following detailed description.

Disclosed herein are embodiments of a method for producing jet-range hydrocarbons from $C_4$ olefins via oligomerization, and the jet-range hydrocarbons produced thereby. As used herein, the term "jet-range hydrocarbons," "jet-range paraffins," or "jet fuel" refers to a composition of hydrocarbons that boil in a range such that the volatility characteristics of the hydrocarbon (or paraffinic form of the hydrocarbon after hydrogenation) that substantially conform to the volatility standards of flash point and distillation range set forth in one or more of the various grades promulgated by ASTM as discussed above. The embodiments described herein reduce the tradeoffs between jet fuel flash point, yield, and freeze point by manipulating the operation of the oligomerization zone of the alcohol-to-jet fuel ("ATJ") production process. In the oligomerization zone, light olefins are oligomerized into the naphtha and distillate boiling ranges. The effluent of the oligomerization reaction is then fractionated such that a naphtha stream is split from jet fuel and heavier effluent. The jet fuel and heavier effluent is sent to downstream processing for saturation, but the naphtha fraction is recycled back to the oligomerization reactor to allow it to react again up into the distillate boiling range. The ATJ oligomerization section is flexible to cut naphtha from the oligomerization effluent as needed to control the downstream jet fuel flash point. The yield of jet fuel does not suffer significantly for two main reasons: 1. ATJ jet fuel, due to its extremely branched nature, has an exceptionally low freeze point well below specification limits, such that there is room for the freeze point to increase closer to the specification limits as flash point is adjusted. 2. The recycle of naphtha to the oligomerization reactor allows the oligomerization reactor operation to be adjusted to optimize the yield of jet fuel such that most of the distillate exiting the oligomerization fractionation section is actually jet fuel, and not heavy product. Accordingly, it is possible to produce JP-5 type jet fuel with very similar yield as when the system is producing JP-8 or Jet A-1.

Reference will hereafter be made to the FIGURE, which schematically illustrates an exemplary system 10 utilizing an exemplary method for producing jet-range hydrocarbons from a mixture of olefins that includes at least C4 olefins. System 10 includes a feedstock source 99, i.e., a source of C4 alcohols that can be dehydrated in a dehydration zone 154 to form C4 olefins. In an alternative embodiment, the feedstock source 99 includes butenes, for example butenes derived from a biorenewable source, in which case the dehydration zone 154 is not needed. In an exemplary embodiment, the renewable butenes are derived from their corresponding alcohols (i.e., C4 alcohols, especially including isobutanol), which are typically formed by fermentation or by condensation reactions of synthesis gas. For example, the feedstock for the fermentation process can be any suitable fermentable feedstock known in the art, such as sugars derived from agricultural crops including sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). In another example, renewable alcohols, such as isobutanols, can be prepared photosynthetically, for example using cyanobacteria or algae engineered to produce isobutanol and/or other alcohols. When produced photosynthetically, the feedstock for producing the resulting renewable alcohols is light, water, and $CO_2$, which is provided to the photosynthetic organism (e.g., cyanobacteria or algae). Additionally, other known methods, whether biorenewable or otherwise, for producing isobutanol are suitable for supplying the feedstock source 99; the methods described herein are not intended to be limited by the use of any particular renewable feed source. C4 olefins form the effluent stream 182 of dehydration zone 154.

Dehydration zone 154, when employed, may be operated according to the following. Suitable dehydration catalysts include homogeneous or heterogeneous catalysts. A non-limiting list of homogeneous acid catalysts include inorganic acids such as sulfuric acid, hydrogen fluoride, fluorosulfonic acid, phosphotungstic acid, phosphomolybdic acid, phosphoric acid, Lewis acids such as aluminum and boron halides (e.g., $AlCl_3$, $BF_3$, etc.); organic sulfonic acids such as trifluoromethanesulfonic acid, p-toluenesulfonic acid and benzenesulfonic acid; heteropolyacids; fluoroalkyl sulfonic acids, metal sulfonates, metal trifluoroacetates, compounds thereof and combinations thereof. A non-limiting list of heterogeneous acid catalysts include heterogeneous heteropolyacids (HPAs); solid phosphoric acid; natural clay minerals, such as those containing alumina or silica; cation exchange resins such as sulfonated polystyrene ion exchange resins; metal oxides, such as hydrous zirconium oxide, $Fe_2O_3$, $Mn_2O_3$, γ-alumina, etc.; mixed metal oxides, such as sulfated zirconia/γ-alumina, alumina/magnesium oxide, etc.; metal salts such as metal sulfides, metal sulfates, metal sulfonates, metal nitrates, metal phosphates, metal phosphonates, metal molybdates, metal tungstates, metal borates; zeolites, such as NaY zeolite, H-ZSM-5, NaA zeolite, etc.; modified versions of any of the above known in the art, and combinations of any of the above.

The dehydration reaction of the processes of the present disclosure, when employed, is typically carried out using one or more fixed-bed reactors using any of the dehydration catalysts described herein. Alternatively, other types of reactors known in the art can be used, such as fluidized bed reactors, batch reactors, catalytic distillation reactors, etc. In a particular embodiment, the dehydration catalyst is a heterogeneous acidic γ-alumina catalyst. In some embodiments, the dehydration reaction is carried out in the vapor phase to facilitate removal of water (either present in the dehydration feedstock or as a by-product of the dehydration reaction). In most embodiments, the dehydration reaction is carried out at a pressure ranging from 0-300 psig, and at a temperature of about 350° C. or less (e.g., about 300-350° C.).

The effluent stream 182 from the dehydration zone 154 is joined with a saturated diluent recycle stream 176 that includes C9-C20 paraffins when the system 10 is operating to produce a JP-8 type specification jet fuel, and C11-C20 paraffins when the system 10 is operating to produce a JP-5 type specification jet fuel. Of course, it will be understood by the person having ordinary skill in the art that these carbon number ranges are approximate, and may vary by one or two numbers up or down in a given embodiment. Further, the effluent from the oligomerization reactor zone 1 continues downstream, a fraction of which forms an olefinic naphtha recycle stream 177 that includes C5-C8 olefins when the system 10 is operating to produce a JP-8 type specification jet fuel, and C5-C10 olefins when the system 10 is operating to produce a JP-5 type specification jet fuel. Greater detail regarding streams 176 and 177 is provided below. Stream 182, combined with streams 176 and 177, is referred to in the FIGURE as combined stream 178. Such combination may be accomplished using a suitable valve/mixing device, apparatus, or other similar means.

The C4-C8 or C10 (depending on the mode of operation) olefins in combined stream 178 are delivered to an oligomerization reaction zone 1 that includes at least an oligomerization reactor. In the oligomerization reaction zone 1, at least a portion of the C4-C8 or C10 olefins are converted into a mixture of heavier boiling hydrocarbons including jet-range hydrocarbons via oligomerization by reacting the C4-C8 or C10 olefins using a zeolitic oligomerization catalyst. Under appropriate conditions zeolitic catalysts such as MTT, TON, MFI, and MTW will yield jet-range hydrocarbons with a broader distribution of components than do non-zeolitic catalysts, such as sulfonated polystyrene resins or solid phosphoric acid catalysts.

As noted, the oligomerization catalyst may include a zeolitic catalyst. The zeolite may include between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. Three-letter codes indicating a zeotype are as defined by the Structure Commission of the International Zeolite Association and are maintained at http://www.iza-structure.org/databases/. UZM-8 is as described in U.S. Pat. No. 6,756,030. In a preferred aspect, the oligomerization catalyst may include a zeolite with a framework having a ten-ring pore structure. Examples of suitable zeolites having a ten-ring pore structure include TON, MTT, MFI, MEL, AFO, AEL, EUO and FER. In one embodiment, the oligomerization catalyst including a zeolite having a ten-ring pore structure may include a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the oligomerization catalyst includes an MTT zeolite.

The oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. An exemplary binder is an aluminum-based binder, such as alumina, aluminum phosphate, silica-alumina and clays.

One of the components of the catalyst binder utilized in the present disclosure is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark Versal. An exemplary alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), for example about 0.79 mm (1/32 inch) to about 6.35 mm (0.25 inch), and most such as about 0.06 mm (1/24 inch) to about 4.23 mm (1/6 inch).

With regard to the oligomerization reaction zone 1 in the FIGURE, process conditions are optimized to produce a higher percentage of jet range hydrocarbon olefins which, when hydrogenated in subsequent steps as will be described below, result in a desirable jet-range hydrocarbon product. In one exemplary embodiment, an MTT-type zeolite catalyst disposed on a high purity pseudo boehmite alumina substrate in a ratio of about 80/20 is provided within the oligomerization reaction zone 1 in the FIGURE. To achieve the most desirable olefin product, the oligomerization reactor is run at a temperature from about 100° C. to about 340° C., and such as from about 180° C. to about 260° C., for example about 210 C to about 240 C. The oligomerization reactor 1 is run at a pressure from about 300 psig to about 1000 psig, and such as from about 690 psig to about 1000 psig. When the oligomerization reaction is performed according to the above-noted process conditions, a $C_4$ olefin conversion of greater than or equal to about 95% is achieved, or greater than or equal to 97%. The resulting product stream 102 includes a plurality of oligomerized olefin products.

The oligomerized olefin products are conveyed to a distillation column 3 via stream 102 where the oligomers that boil lighter than the jet range hydrocarbons are separated from the jet-range hydrocarbons. When the desired specification of jet fuel is the JP-8 type, the separated hydrocarbons are typically, but not limited to, in the C5-C8 range. When the desired specification of jet fuel is the JP-5 type, the separated hydrocarbons are typically, but not limited to, in the C5-C10 range. These separated hydrocarbons are removed from the distillation column 3 as naphtha recycle stream 173, which is an olefinic recycle stream taken as an upper side cut from distillation column 3. Additionally, any lighter components that may be present, such as C4-components, are removed from the overhead of column 3 via stream 172. A small fraction, such as less than 20%, or less than 10%, of naphtha recycle stream 173 is removed from the system 10 as a purge stream 174. The balance of stream 173 continues as olefinic recycle stream 177, which as noted above joins with stream 182 (C4 olefins) prior to oligmerization, and may be joined by stream 176. Accordingly, the effluent of the oligomerization reaction is fractionated such that the naphtha stream 173 is split from jet fuel and heavier effluent (stream 175). The jet fuel and heavier effluent is sent to downstream processing for saturation as discussed below, but the naphtha fraction is recycled back to the oligomerization reactor to allow it to react again up into the distillate boiling range as noted above. The ATJ oligomerization section is flexible to cut naphtha from the oligomerization effluent as needed to control the downstream jet fuel flash point. The recycle of naphtha to the oligomerization reactor allows the oligomerization reactor operation to be adjusted to optimize the yield of jet fuel such that most of the distillate exiting the oligomerization fractionation section is actually jet fuel, and not heavy product.

Accordingly, distillation bottoms stream 175 includes approximately C9-C20 olefins when the system 10 is operating to produce a JP-8 type specification jet fuel, and approximately C11-C20 olefins when the system 10 is operating to produce a JP-5 type specification jet fuel. Bottoms stream 175 is then sent for further downstream processing, which includes hydrogenation of olefins to paraffins. Hydrogenation is carried out in hydrogenation zone 191 in the presence of a suitable active metal hydrogenation catalyst. Acceptable solvents, catalysts, apparatus, and procedures for hydrogenation in general can be found in Augustine, Heterogeneous Catalysis for the Synthetic Chemist, Marcel Decker, New York, N.Y. (1996). Many hydrogenation catalysts known in the art are effective, including (without limitation) those containing as the principal component iridium, palladium, rhodium, nickel, ruthenium, platinum, rhenium, compounds thereof, combinations thereof, and the supported versions thereof.

The hydrogenation zone 191 produces and effluent stream 192 that includes approximately C9-C20 paraffins when the system 10 is operating to produce a JP-8 type specification jet fuel, and approximately C11-C20 paraffins when the system 10 is operating to produce a JP-5 type specification jet fuel. A portion of stream 192, for example from about 0% to about 50%, such as about 10% to about 20%, is recycled back to join the C4 olefins stream 182 prior to oligomerization as the aforementioned saturated diluent recycle stream 176. In other embodiments, the percentage may be 0-50%, 0-30%, or 10-20%. A suitable stream diversion device/apparatus, or similar means, may be employed for this purpose. The balance of stream 192 continues as stream 194 to fractionation column 195. In fractionation column 195, the jet fuel product, whether of the JP-8 type (~C9-~C20 paraffins) or the JP-5 type (~C11-~C20 paraffins), is separated as a fractionation column overhead stream 196 from any heavier (i.e., C20+) hydrocarbons that may be present in the stream 194. The heavier hydrocarbons are removed from system 10 as a fractionation column bottoms product via stream 197.

Accordingly, the described methods and systems reduce the tradeoffs between jet fuel flash point, yield, and freeze point by manipulating the operation of the oligomerization zone of the alcohol-to-jet fuel ("ATJ") production process. In the oligomerization zone, light olefins are oligomerized into the naphtha and distillate boiling ranges. The effluent of the oligomerization reaction is then fractionated such that a naphtha stream is split from jet fuel and heavier effluent. The jet fuel and heavier effluent is sent to downstream processing for saturation, but the naphtha fraction is recycled back to the oligomerization reactor to allow it to react again up into the distillate boiling range. The ATJ oligomerization section is flexible to cut naphtha from the oligomerization effluent as needed to control the downstream jet fuel flash point. The recycle of naphtha to the oligomerization reactor allows the oligomerization reactor operation to be adjusted to optimize the yield of jet fuel such that most of the distillate exiting the oligomerization fractionation section is actually jet fuel, and not heavy product. As such, it is possible to produce JP-5 type jet fuel with very similar yield as when the system is producing JP-8.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for producing jet-range hydrocarbons comprising the steps of:
    combining a first stream comprising C4 olefinic hydrocarbons and a second stream comprising at least 75 wt. % C5-C10 olefinic hydrocarbons to produce a third stream
    comprising C4-C10 olefinic hydrocarbons;
    oligomerizing the third stream comprising C4-C10 olefinic hydrocarbons to produce a fourth stream comprising C4-C20 olefinic hydrocarbons wherein the step of oligomerizing is performed using a zeolite catalyst comprising a TON, MTW, or MTT zeolite supported on a binder comprising a pseudo boehmite alumina substrate:
    separating C5-C10 hydrocarbons from the fourth stream comprising C4-C20 olefinic hydrocarbons to produce the second stream and a fifth stream comprising C11-C20 olefinic hydrocarbons; and
    hydrogenating the fifth stream comprising C11-C20 olefinic hydrocarbons to produce a sixth stream comprising C11-C20 paraffinic jet-range hydrocarbons having a flash point as measured by ASTM D93 of about 60° C.

2. The method of claim 1, further comprising dehydrating a stream comprising C4 alcohols to form the first stream comprising C4 olefinic hydrocarbons.

3. The method of claim 2, wherein the C4 olefinic hydrocarbons are derived from dehydrating a renewable alcohol with a $^{14}C/^{12}C$ isotope ratio indicative of atmospheric carbon.

4. The method of claim 1, further comprising recycling a portion of the sixth stream comprising C11-C20 paraffinic jet-range hydrocarbons to combine with the first and second streams prior to the step of oligomerizing.

5. A method for producing jet-range hydrocarbons comprising the steps of:

combining a first stream comprising C4 olefinic hydrocarbons and a second stream comprising C5-C10 olefinic hydrocarbons to produce a third stream comprising C4-C10 olefinic hydrocarbons;

oligomerizing the third stream comprising C4-C10 olefinic hydrocarbons in presence of an MTT zeolite catalyst on a pseudo boehmite alumina substrate in a ratio of about 80/20 of catalyst to substrate to produce a fourth stream comprising C4-C20 olefinic hydrocarbons;

separating C5-C10 hydrocarbons from the fourth stream comprising C4-C20 olefinic hydrocarbons to produce the second stream and a fifth stream comprising C11-C20 olefinic hydrocarbons; and hydrogenating the fifth stream comprising C11-C20 olefinic hydrocarbons to produce a sixth stream comprising C11-C20 paraffinic jet-range hydrocarbons.

* * * * *